United States Patent [19]
Berendt et al.

[11] Patent Number: 4,818,226
[45] Date of Patent: Apr. 4, 1989

[54] ORTHODONTIC ARCHWIRE

[75] Inventors: Carl J. Berendt, Carlsbad; Gerald Nelson; Michael Meyer, both of Berkeley, all of Calif.

[73] Assignee: Lancer Pacific, Carlsbad, Calif.

[21] Appl. No.: 98,615

[22] Filed: Sep. 18, 1987

[51] Int. Cl.[4] .............................................. A61C 7/00
[52] U.S. Cl. ....................................................... 433/20
[58] Field of Search ................................... 433/20, 22

[56] References Cited

U.S. PATENT DOCUMENTS 4,268,250  5/1981  Reeve .................................... 433/20

FOREIGN PATENT DOCUMENTS 2910021  9/1979  Fed. Rep. of Germany ........ 433/20

OTHER PUBLICATIONS

"Nitinol Activ. Arch" 4 pages May 7, 1979.

Primary Examiner—Robert Peshock
Attorney, Agent, or Firm—Fulwider, Patton, Lee & Utecht

[57] ABSTRACT

An orthodontic archwire having a specific, saddle-like configuration and being composed of a near-stoichiometric alloy of nickel and titanium which possesses memory retaining characteristics, the archwire having a first, second and third curved section, wherein the first and second curved sections include two different radii of curvature which extend distally from the midline of the archwire, and the third curved section includes two radii of curvature extending distally from the midline of the archwire, so that the preset form of the archwire resembles a saddle-like configuration.

17 Claims, 2 Drawing Sheets

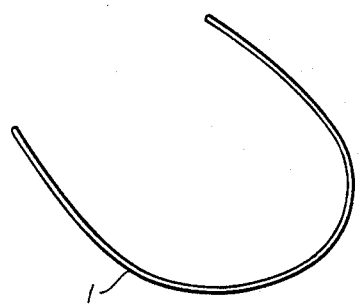
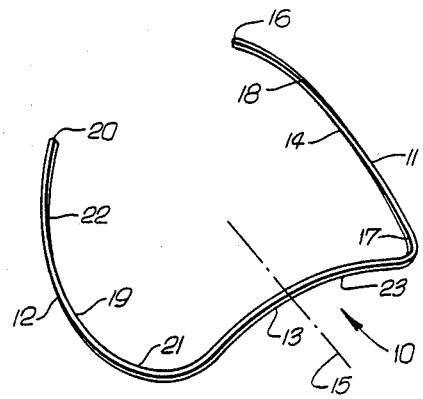
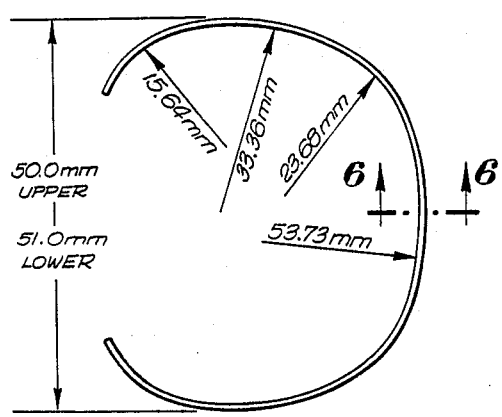
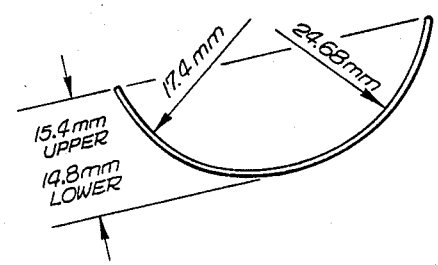
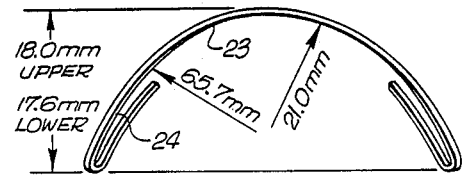

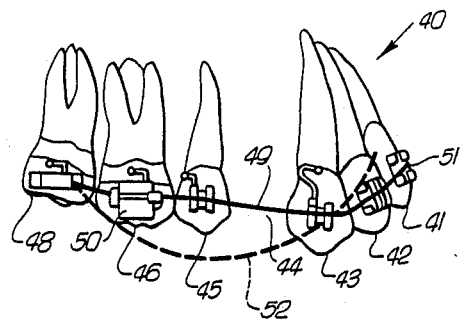
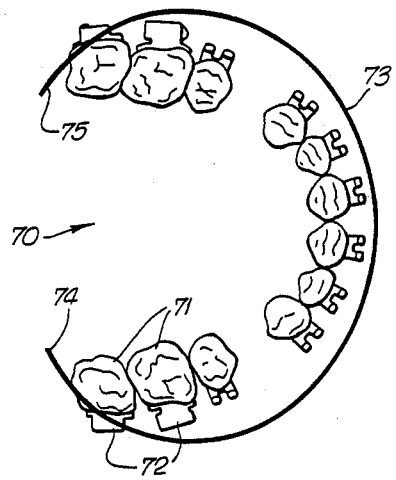
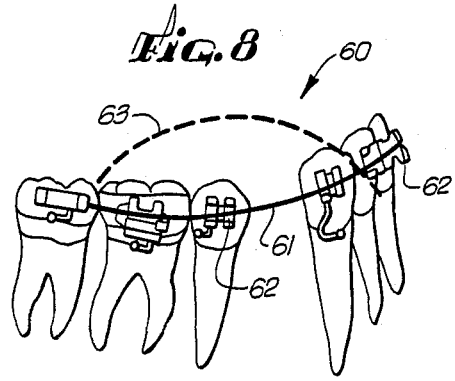
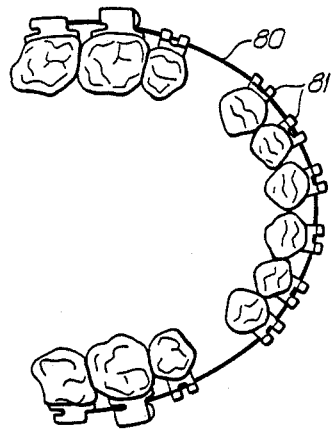
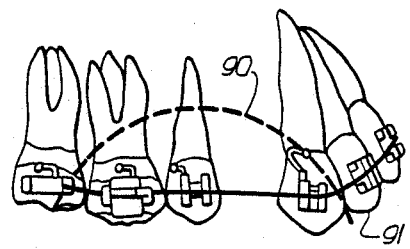

ORTHODONTIC ARCHWIRE

FIELD OF THE INVENTION

A nickel and titanium alloy archwire having a saddle-like configuration which imparts counterforce mechanics for the orthodontic treatment in moving and positioning teeth.

BACKGROUND OF THE INVENTION

A rocking chair shape archwire was first developed by hand by clinicians in round cross-section, stainless steel archwires to correct or negate the oral forces necessary to produce the curve of spee. Another name used for the reverse curve of spee arch is the "M" arch, named after Dr. Margolias of Boston University. The M arch was used by clinicians from the 1960's throughout the early 1980's for early treatment of typical malocclusions with deep overbites often with wide diastemas mixed dentition between the maxillary incisors, and generally for retraction and intrusion of same.

Each M archwire was custom handcrafted on an individual patient basis since there were none commercially available in a standardized configuration. Thus, clinicians were involved in time consuming hand fabrication of an M arch for each patient. In an article entitled "The M Arch", by Jerome L. Blafer, D.D.S., M arch is described as basically a wire with an exaggerated curve of spee and exaggerated molar contraction bends. It could be used in conjunction with coil springs on the arch to complete the basic force system. Further, clinicians using the M arch treatment necessarily had to see their patients at approximately 3–4 week intervals, at which time the arch could be reformed, i.e., new force moments could be incorporated into the archwire so that there would be new forces imparted to continue the movement of the teeth to a desired position. Over the course of a few weeks, the round stainless steel M archwire would gradually loose its ability to impart forces to the teeth so that at the end of the 3–4 week period, the archwire had to be reshaped to impart new forces. Also, the M archwire generally required use of elastics, looping devices, and head gear to enhance the movement of teeth to the desired position.

Other prior art appliances used to position teeth included curved archwires, archwires with loops, and archwires having a generally U-shaped configuration. Such archwires are more fully disclosed in U.S. Pat. Nos. 4,268,250, 4,097,993, and 4,197,643. Some of the prior art archwires required closing loops bent into the archwire. Such looped wires had inherently less control in moving teeth as compared to a solid wire. Loss of tip and rotational control adjacent to the loops can occur and arch form and occlusal plane control is not optimum. Loops tend to trap plaque and food debris and can create soft tissue irritation. Activation and adjustment of loop systems, usually at three to four week intervals, can be troublesome. Fabrication, placement and removal of these systems are often time consuming. Re-leveling and root uprighting are often necessary to regain complete control as the finishing treatment stages begin.

The prior art also includes U.S. Pat. No. 4,037,324, which discloses the use of an archwire having a specific chemical composition which wire cause the archwire to return to a preset shape or length after being deformed and then heated. The mechanical memory of the wire will tend to restore the will to a preset shape upon heating in order to level or torque malposed teeth. The prior art wires are formed of a Nitinol alloy which is a known near-stoichiometric alloy of nickel and titanium. The alloy may also include cobalt substituted for nickel on an atom-for-atom basis so that the composition is $TiNi_{0.935}Co_{0.065}$. Even though the prior art discloses an archwire composition having desirable memory retaining qualities, it does not fully utilize the advantages of such qualities.

The primary object of the present invention is to provide an archwire to move teeth en masse by configuring the archwire so that as it returns to a preset shape, it will provide low, continual forces to the teeth to position them in the desired manner.

It is a further object of the invention to provide a pre-formed archwire having a specific configuration and which is composed of a near-stoichiometric alloy of nickel and titanium so that after attaching it to orthodontic brackets, the archwire will gradually move teeth to their desired position as it returns to its preset shape.

It is an important object of the invention to provide a pre-formed archwire of a specific configuration which incorporates zero plane mechanics so that as the arch is pressed flat at its midline and rocked slowly toward the posterior ends of the archwire, the archwire will remain flat on the surface. This characteristic prevents axial or tortional forces along the long axis of the archwire which would have a tendency to rotate teeth in the facial or lingual direction, i.e. undesirable tipping of roots.

Another object of the invention is to reduce the chair time required by patients in using the prior art devices.

It is a further object of the invention to provide a pre-formed archwire of a specific configuration and composition which the clinician cannot change by re-working or reshaping the archwire.

It is another object of the invention to provide an archwire having reduced frictional forces to permit the brackets to slide easily along the archwire.

It is a still further object of the invention to provide a pre-formed archwire of a specific configuration having a moment-to-force ratio of about 10:1 for closure of spaces without experiencing the adverse aspect of "dumping" or the rotation of a tooth root into an extraction site.

These and other objects will be pointed out and described in further detail hereinafter.

SUMMARY OF THE INVENTION

The orthodontic archwire according to the invention is a pre-formed wire having a specific, saddle-like configuration and being composed of a near-stoichiometric alloy of nickel and titanium which possess memory retaining characteristics, the archwire having a first, second and third curved section, wherein the first and second curved sections include two different radii of curvature which extend distally from the midline of the archwire, and the third curved section includes two radii of curvature extending distally from the midline of the archwire, so that the preset form of the archwire resembles saddle-like configuration. The archwire is mounted in slots incorporated in orthodontic brackets which are fastened to the teeth. The archwire, due to its memory retaining characteristics, will attempt to return to its pre-formed configuration, and in so doing will provide a low and continual force to the teeth, thereby moving the teeth to their desired locations.

A more complete understanding of the invention will be obtained from the following detailed description and from the accompanying drawing figures illustrating the invention and the relationship of the elements described and exemplified herein.

BRIEF DESCRIPTION OF THE DRAWINGS

FIG. 1 is a perspective view of a prior art archwire similar to the one disclosed in U.S. Pat. No. 4,097,993;

FIG. 2 is a perspective view of an unstressed archwire of the present invention depicting the pre-formed configuration having a saddle-like appearance;

FIG. 3 is side view of the archwire in its unstressed condition where the anterior portion of the archwire is at the right hand side of the drawing figure, and the posterior portion of the archwire is on the left hand side of the drawing figure;

FIG. 4 is a front view of the archwire in its unstressed condition;

FIG. 5 is a top view of the archwire as it would appear if it were compressed onto a flat surface;

FIGS. 6a, 6b and 6c are cross-sectional views of the archwire of FIG. 5 taken substantially along the line 6—6 wherein the archwire may have a square, rectangular, or round cross-section;

FIG. 7 is a fragmentary partly schematic elevational view illustrating the operation of the invention in relation to the upper teeth and jaw;

FIG. 8 is a fragmentary partly schematic elevational view illustrating the operation of the invention in relation to the lower teeth and jaw;

FIG. 9 is a plan view of the upper jaw illustrating the toe in at the posterior segment;

FIG. 10 is a plan view of the upper jaw illustrating a wide arch form; and

FIG. 11 is a fragmentary partly schematic elevational view illustrating the operation of the invention by reversing the curve.

DETAILED DESCRIPTION OF THE INVENTION

Due to the configuration and composition of the archwire of the present invention it is possible to move all of the teeth en masse to their desired locations. In general, the present invention includes a nickel-titanium alloy archwire having a preset, saddle-like configuration which imparts counterforce mechanics to various orthodontic cases which require closing of spaces, opening and closing bites, consolidating arches, arch expansion, retracting protrusive incisors in mixed dentition, and closing diastemas. Correction of these malocclusions is not always possible or is at least very complicated when using prior art appliances. For example, in FIG. 1, there is shown a prior art archwire 1 which is substantially similar to that disclosed in U.S. Pat. No. 4,097,993. The limitations of archwire 1 are readily apparent in that all of the teeth cannot be moved at the same time and there are no counterforces to intrude or extrude dentition. The prior art archwires must rely on elastics, looping devices, ligature wires, and other such appliances to move one or several teeth at the same time to a desired location. Further, such devices are subjected to high occusal forces which can reshape the archwire and cause undesired movement of teeth.

Turning to FIG. 2, there is shown the preferred embodiment of the present invention. The archwire 10 has a number of compound curves giving it a saddle-like configuration which has been pre-formed through a number of manufacturing processes such that the archwire has memory retaining characteristics. It is preferred that archwire 10 be composed of a near-stoichiometric alloy of nickel and titanium substantially similar to that disclosed U.S. Pat. No. 4,037,324. The particular composition of titanium, nickel, and in some instances colbalt, provide the memory retaining characteristics of archwire 10 such that it will always try to return to its pre-formed condition after it has been mounted on orthodontic brackets. By slowly and continually attempting to return to its pre-formed condition, archwire 10 will impart forces to the teeth to move them to a desired location.

As is shown in FIGS. 1—4, archwire 10 is comprised of a first curved section 11, a second curved section 12, and a third curved section 13. The length of archwire comprising each of the curved sections 11, 12, and 13, essentially form three intersecting planes.

Turning to first curved section 11, it comprises a length of archwire 14 which extends from substantially the midline 15 of archwire 10 and extends distally along archwire section 14 to end 16. First curved section 11 is comprised of two radii of curvature having different values, wherein the first radii of curvature 17 is smaller than second radii of curvature 18.

Similarily, second curved section 12 is comprised of archwire section 19 which extends distally from the midline 15 of archwire 10 to end 20. Second curved section 12 is comprised of two different radii of curvature wherein the first radius of curvature 21 is smaller than the second radii of curvature 22. It is intended that first radius of curvature 17 and first radius of curvature 20 be substantially equal. Further, it is intended that second radius of curvature 18 and second radius of curvature 22 also be substantially equal to one another. Uniformity in the first and second curved sections is essential to insure the uniform movement of the teeth. In other words, if the first and second curved sections where not essentially mirror images of each other, the teeth on one side of the midline would tend to locate in different positions relative to the teeth on the other side of the midline.

With respect to third curved section 13, it is comprised of two radii of curvature wherein first radius of curvature 23 is substantially smaller than second radus of curvature 24. For most applications it is intended that second radius of curvature 23 be approximately three times greater than first radius of curvature 23.

It is noted that in FIGS. 2-4, archwire 10 and its corresponding curved sections, is illustrated in its unstressed or relaxed state. In its relaxed state the archwire is designed to have a specific configuration for both the upper and lower arch such that the archwire will provide a more natural curve of spee after treatment.

Also illustrated in FIGS. 3 and 4 are several examples of desired radii of curvature for both the upper and lower jaw. Thus, in FIG. 3, first radii of curvature 17 and 21 have a value of 24.68 millimeters (mm), second radii of curvature 18 and 22 are 17.4 mm, first radius of curvature 23 is 21.0 mm, and second radius of curvature 24 is 65.7 mm. As is generally the case, the upper archwire is slightly larger than the lower archwire as illustrated.

Turning to FIG. 5, archwire 10 is illustrated in a flattened condition much as it would appear if, for example, it was compressed onto a flat surface. As is shown, the archwire in this position appears as a series of trifocal ellipses having various radii of curvature. As is shown, specific values of radii of curvature are illustrated and these values substantially correspond to the values illustrated in FIGS. 3 and 4. The specific values illustrated in FIGS. 3–5 are intended as examples only and are not to be viewed as limitations. The following chart sets forth the claimed ranges of values for the various radii of curvature.

|  | minimum radius (mm) | maximum radius (mm) |
|---|---|---|
| first radius of curvature 17 | 21.0 | 27.0 |
| second radius of curvature 18 | 15.0 | 20.0 |
| first radius of curvature 21 | 21.0 | 27.0 |
| second radius of curvature 22 | 15.0 | 20.0 |
| first radius of curvature 23 | 19.0 | 25.0 |
| second radius of curvature 24 | 60.0 | 75.0 |

Certain advantages are achieved when using an archwire having a specific cross-section. Thus, as shown in FIGS. 6a, 6b, and 6c, the archwire of the invention can be round, rectangular, or square. A rectangular wire will normally fit better in the slots found in orthodontic brackets, thereby reducing "slot play" which may affect the archwire's ability to rotate a tooth. Also, the rectangular archwires of the present invention has been designed to incorporate zero plane mechanics. As the archwire is pressed flat at its midline, and rocked slowly toward its distal ends, the wire remains at all times flat. When mounted on brackets, this characteristic prevents axial or torsional force along the long axis of the wire which would have a tendency to rotate the teeth in the facial or lingual direction.

Rectangular wires used for retraction have the following dimensions, all in inches: 0.016×0.022 and 0.017×0.025 for 0.018 slot appliances and 0.019×0.025 and 0.021×0.025 for 0.022 slot appliances. Each of these wires nearly fills the bracket slot. As discussed, minimal slot play enhances torque control and allows nearly full expression of built-in bracket adjustments. Sliding mechanics on comparably-sized stainless steel wires would create large frictional forces while using nickel and titanium alloy wires allows nearly full-sized wires to be used without creating large frictional forces. To reduce friction in stainless steel wire sliding systems the wire dimension must be decreased. This leads to excessive slot play, loss of torque control, and increased risk of deformation due to high occusal forces.

Clinical application of the present invention may vary somewhat depending upon the various orthodonic cases and the desired results. FIGS. 7-11 illustrate various clinical applications of the invention.

Turning to FIG. 7, there is shown an upper jaw portion 40 having a central incisor 41, a lateral incisor 42, a cuspid 43, an extraction site 44, a second bicuspid 45 and a pair of molars 46 and 48. Archwire 49 is shown as it is mounted on a series of orthodontic brackets 50 which are fixed to the teeth by a known method (a bonding epoxy or resin). In order to securely mount archwire 49 onto the orthodonic bracket 50, each bracket is equipped with slots 51 in which archwire 49 is contained. Ligature wires (not shown) or other appliances which are generally known may be used to securely fasten archwire 49 in slots 51. In its mounted position, archwire 49 has been bent from its unstressed condition in order to be mounted in slots 51. Archwire 52 represents the invention as it would appear in its unstressed condition, and as treatment of the patient continues, archwire 49 will attempt to return to its preset condition as illustrated by archwire 52. In doing so, the illustrated teeth will move to a desired location. As illustrated in FIG. 7, archwire 49 will counter posterior extrusion tendencies, the tooth crowns will not tip towards each other, the tooth roots will not dump or fall into extraction site 44, and the bite is simultaneously opened while extrusive force is countered. Further, with the use of elastomeric chains (not shown) stretched over each bracket 50, retraction of the six anteriors is accomplished en masse.

As is shown, by intruding molars 46 and 48 and incisors 41 and 42 while simultaneously extruding bicuspids 45 and cuspids 43, favorable changes occur in the anterior vertical dimension that permit a subsequent reduction in anterior overjet with retraction mechanics. Without incisor intrusion, it is often impossible to control the horizontal position of the dentition. But when the incisors are properly intruded, more effective horizontal overjet is created that permits distalization of the upper arch or more anterior displacement of the lower arch and teeth.

An advantage not readily apparent from the drawing figure is that due to the composition of archwire 49, i.e. a nickel and titanium alloy, there is a reduced amount of friction between archwire 49 and slots 51 than that experienced by prior art stainless steel archwires. Where there is no angulation in the wire between the bracket and the archwire, there is no significant difference between stainless steel and nickel and titanium alloy wires as to the amount of force needed to start the movement of a bracket over the wire. However, as angulation between the bracket and the archwire increases from about 5 to 15 degrees, stainless steel wires require an increasing amount of force to overcome friction when compared to nickel and titanium alloy archwires. For a further discussion see "A Comparison of Friction Resistance for Nitinol and Stainless Steel Wire in Edgewise Brackets," by Peterson, et al.

Thus, a given nickel and titanium wire generates significantly less frictional force than a comparably sized stainless steel wire in a situation where there is binding friction from orthodonic brackets tipped against the archwire. This should not be confused with static friction as measured in a non-tipped bracket. Nickel and titanium wires exhibit slightly greater static friction than comparably sized stainless steel wires. Lower frictional force means a more continuous level of tooth moving force delivered to the teeth during each appointment interval.

Turning to FIG. 8 there is a lower jaw portion 60 having a number of teeth and an archwire 61 mounted on orthodontic brackets 62 similar to that described for FIG. 7. Again, archwire 63 appears in its unstressed condition while archwire 61 will slowly, over time, impart forces to the teeth as it attempts to return to its unstressed condition as shown by archwire 63. Due to the configuration of archwire 61 as claimed, excessive mandibular curve of spee is eliminated so that as the teeth reach their permanent position, a more natural curve of spee is achieved.

Turning to FIG. 9, there is shown a jaw portion 70 having a number of teeth 71 and orthodontic brackets 72 mounted on the teeth. An archwire 73 is illustrated with its posterior ends 74, 75 turned inwardly toward the midline of the arch. This condition is referred to as "toe in" which will prevent mesio-lingual rotation of the distal most molar on each side of the midline. The arch form of the invention is accentuated to counteract the tendency for the most distal tooth to rotate mesio-lingually under the influence of an elastomeric chain if one is used, for example, for retraction. There is also a tendency for the teeth and the buccal segments to tip toward the lingual as space closure proceeds. The accentuated width of the archwire places a buccal-tipping moment in the buccal segment that counteracts the lingual-tipping tendency. Therefore arch form integrity is maintained.

FIG. 10 illustrates an archwire 80 mounted on brackets 81 wherein a wide arch form will counter lingual crown tipping.

Very often the practicing clinician is confronted with an anterior open bite or such a condition may develop during treatment. The invention is particularly useful, as illustrated in FIG. 11, in closing an anterior open bite. By reversing the curved archwire 90 (unstressed), the incisors 91 can be extruded and a more acceptable overbite can be achieved for patients who start with an anterior open bite or who develop one during treatment.

Although not shown in the drawings, the archwire claimed herein may be used on the lingual side of the teeth. Mounting on the lingual side is difficult and time consuming, but offers the advantage of nearly invisible orthodontics. Some patients may request lingual mounting, in such cases the archwire as claimed would preform substantially as described herein to correct various malocclusions.

Those skilled in the art realize that various modifications, adaptations and variations of the foregoing specific embodiments can be made without departing from the spirit and scope of the present invention. Thus, it is emphasized that the invention is not limited to the particular embodiments disclosed, but is defined by the claims as follows.

What is claimed is:

1. An orthodontic archwire of unitary memory retaining wire for repositioning teeth en masse, the archwire comprising a first, second and third curved section, the first curved section extending distally from a midline and having at least two different radii of curvature along its length when the archwire is in an unstressed condition, the second curved section extending distally from the midline of the archwire in a direction opposite of the first curved section and having at least two different radii of curvature along its length when the archwire is in an unstressed condition, and the third curved section extending distally in opposite directions from the midline of the archwire and having at least two radii of curvature when the archwire is in an unstressed condition, whereby the archwire, when mounted on orthodontic brackets, applies continual force throughout treatment to move and position teeth by utilizing counterforce mechanics.

2. The orthodontic archwire as defined in claim 1, wherein one radius of curvature of the first and second curved sections is larger than the other radius of curvature.

3. The orthodontic archwire as defined in claim 1, wherein one radius of curvature of the first and second curved sections ranges between 15.0 and 20.0 millimeters and the second radius of curvature of the first and second curved sections ranges between 21.0 and 27.0 millimeters.

4. The orthodontic archwire as defined in claim 1, wherein the first radius of curvature of the third curved section extends along the archwire in opposite directions from the midline to approximately the location of the first cuspids, and the second radius of curvature of the third curved section extends along the archwire distally from about the location of the premolars to about the location of the first molar.

5. The orthodontic archwire as defined in claim 1, wherein one radius of curvature of the third curved section ranges between 19.0 and 25.0 millimeters, and the other radius of curvature of the third curved section ranges between 60.0 and 75.0 millimeters.

6. An orthodontic archwire comprising a unitary memory retaining wire having a saddle-like configuration, the archwire comprising a first, second, and third curved section, the first and second curved sections extending along the archwire in opposite directions distally from a midline, each section having two different radii of curvature along their length when the archwire is in its unstressed condition, and the third curved section extending distally from the midline and having at least two radii of curvature when the archwire is in its unstressed condition, whereby the archwire when mounted on orthodontic brackets, applies continual force throughout treatment to move and position teeth by utilizing counterforce mechanics.

7. The orthodontic archwire as defined in claim 6, wherein one radius of curvature of the third curved section is at least three times greater than the other radius of curvature of the third curved section.

8. An orthodontic archwire of unitary memory retaining wire for repositioning teeth en masse, the archwire comprising a first, second and third curved section, the first and second curved sections extending in opposite directions distally from a midline and each having at least two radii of curvature along their length when the archwire is in an unstressed condition, and the third curved section extending distally from the midline and having at least two radii of curvature when the archwire is in its unstressed condition, whereby the archwire, when mounted on orthodontic brackets, applies continual force throughout treatment to move and position teeth by utilizing counterforce mechanics.

9. The orthodontic archwire of claim 8, wherein the two radii of curvature of each of the first and second curved sections are substantially equal.

10. An orthodontic archwire of unitary memory retaining wire for repositioning teeth en masse, the archwire having a saddle-like configuration and comprising:
 a. first means for providing bite opening while counteracting the posterior extrusive force tendency;
 b. second means to prevent tooth crowns from tipping towards each other during space closure;
 c. third means for preventing excessive curve of spee;
 d. fourth means for correcting excessive curve of spee;
 e. fourth means for counteracting lingual crown tipping; and
 f. fifth means for preventing mesio-lingual rotation of molars during space closure;

whereby the archwire is mounted on orthodontic brackets to apply continual force to achieve space closure while counteracting common side effects.

11. An orthodontic archwire of unitary memory retaining wire for repositioning teeth en masse, the archwire comprising a first, second and third curved section, the first curved section extending distally from a midline and having at least two different radii of curvature along its length when the archwire is in an unstressed condition, the second curved section extending distally from the midline of the archwire in a direction opposite to the first curved section and having at least two different radii of curvature along its length when the archwire is in an unstressed condition, and the third curved section extending distally in opposite directions from the midline of the archwire and having at least two radii of curvature when the archwire is in an unstressed condition, the archwire further having a substantially circular cross-section, whereby the archwire, when mounted on orthodontic brackets, applies continual force throughout treatment to move and position teeth by utilizing counterforce mechanics.

12. An orthodontic archwire of unitary memory retaining wire for repositioning teeth en masse, the archwire comprising a first, second and third curved section, the first curved section extending distally from a midline and having at least two different radii of curvature along its length when the archwire is in an unstressed condition, the second curved section extending distally from the midline of the archwire in a direction opposite of the first curved section and having at least two different radii of curvature along its length when the archwire is in an unstressed condition, and the third curved section extending distally in opposite directions from the midline of the archwire and having at least two radii of curvature when the archwire is in an unstressed condition, the archwire further having a substantially square cross-section, whereby the archwire, when mounted on orthodontic brackets, applies continual force throughout treatment to move and position teeth by utilizing counterforce mechanics.

13. An orthodontic archwire of unitary memory retaining wire for repositioning teeth en masse, the archwire comprising a first, second and third curved section, the first curved section extending distally from a midline and having at least two different radii of curvature along its length when the archwire is in an unstressed condition, the second curved section extending distally from the midline of the archwire in a direction opposite of the first curved section and having at least two different radii of curvature along its length when the archwire is in an unstressed condition, and the third curved section extending distally in opposite directions from the midline of the archwire and having at least two radii of curvature when the archwire is in an unstressed condition, the archwire further having a substantially rectangular cross-section, whereby the archwire, when mounted on orthodontic rackets, applies continual force throughout treatment to move and position teeth by utilizing counterforce mechanics.

14. An orthodontic archwire of unitary memory retaining wire for repositioning teeth en masse, the archwire comprising a first, second and third curved section, the first curved section extending distally from a midline and having at least two different radii of curvature along its length when the archwire is in an unstressed condition, the second curved section extending distally from the midline of the archwire in a direction opposite of the first curved section and having at least two different radii of curvature along its length when the archwire is in an unstressed condition, and the third curved section extending distally in opposite directions from the midline of the archwire and having at least two radii of curvature when the archwire is in an unstressed condition, the composition of the archwire being a near-stoichiometric alloy of nickel and titanium so that the archwire, when mounted on orthodontic brackets, applies a continual, low force component to close space and reposition teeth.

15. An orthodontic archwire of unitary memory retaining wire for repositioning teeth en masse, the archwire comprising a preformed first, second and third curved section, the first curved section extending distally from a midline and having at least two different radii of curvature along its length when the archwire is in an unstressed condition, the second curved section extending distally from the midline of the archwire in a direction opposite of the first curved section and having at least two different radii of curvature along its length when the archwire is in an unstressed condition, and the third curved section extending distally in opposite directions from the midline of the archwire and having at least two radii of curvature when the archwire is in an unstressed condition, the composition of the archwire is a near stoichiometric alloy of nickel and titanium so that the curved sections of the archwire, when mounted on orthodontic brackets, apply continual force components throughout treatment to move and position teeth by attempting to return to their pre-formed condition.

16. An orthodontic archwire of unitary memory retaining wire for repositioning teeth en masse, the archwire comprising a first, second and third curved section, the first curved section extending distally from a midline and having at least two different radii of curvature along its length when the archwire is in an unstressed condition, the second curved section extending distally from the midline of the archwire in a direction opposite of the first curved section and having at least two different radii of curvature along its length when the archwire is in an unstressed condition, and the third curved section extending distally in opposite directions from the midline of the archwire and having at least two radii of curvature when the archwire is in an unstressed condition, the archwire having a substantially rectangular cross-section along its length so that as the archwire is pressed onto a flat surface at its midline, and then rotated along the first and second curved sections, the longest side of the rectangular cross-section will remain in contact with the flat surface.

17. An orthodontic archwire having a preset, saddle-like configuration and composed of a near-stoichiometric alloy of nickel and titanium having memory retaining characteristics, the archwire comprising a first, second and third curved section, the first curved section extending distally from a midline and having at least two different radii of curvature along its length when the archwire is in an unstressed condition, the second curved section extending distally from the midline of the archwire in a direction opposite of the first curved section and having at least two different radii of curvature along its length when the archwire is in an unstressed condition, and the third curved section extending distally in opposite directions from the midline of the archwire and having at least two radii of curvature when the archwire is in an unstressed condition, whereby the archwire, when mounted on orthodontic brackets, applies continual force throughout treatment to move and position teeth by utilizing counterforce mechanics.

* * * * *

UNITED STATES PATENT AND TRADEMARK OFFICE
CERTIFICATE OF CORRECTION

PATENT NO. : 4,818,226

DATED : April 4, 1989

INVENTOR(S) : Carl Berendt; Gerald Nelson; Michael Meyer

Page 1 of 2

It is certified that error appears in the above-identified patent and that said Letters Patent is hereby corrected as shown below:

Col. 1, line 39 delete "loose" and insert --lose--.

Col. 4, line 33 delete "20" and insert --21--.

Col. 4, line 47 delete "23" and insert --24--.

Col. 4, line 45 delete "radus" and insert --radius--.

Col. 5, line 54 delete "orthodonic" and insert --orthodontic--.

Col. 5, line 61 delete "orthodonic" and insert --orthodontic--.

Col. 5, line 64 delete "orthodonic" and insert --orthodontic--.

Col. 6, line 47 delete "orthodonic" and insert --orthodontic--.

Col. 6, line 57 delete "orthodonic" and insert --orthodontic--.

Col. 6, line 67 delete "orthodonic" and insert --orthodontic--.

Col. 7, line 22 delete "(unstressted) and insert--(unstressed)--

Col. 7, line 32 delete "preform" and insert --perform--.

UNITED STATES PATENT AND TRADEMARK OFFICE
CERTIFICATE OF CORRECTION

PATENT NO. : 4,818,226

DATED : April 4, 1989

INVENTOR(S) : Carl Berendt et al

Page 2 of 2

It is certified that error appears in the above-identified patent and that said Letters Patent is hereby corrected as shown below:

Col. 10, line 22 delete "near stoichiometric" and insert --near-stoichiometric--.

Signed and Sealed this

Twenty-fourth Day of October, 1989

*Attest:*

DONALD J. QUIGG

*Attesting Officer*

*Commissioner of Patents and Trademarks*